US005591174A

United States Patent [19]
Clark et al.

[11] Patent Number: 5,591,174
[45] Date of Patent: Jan. 7, 1997

[54] MICROKERATOME AND METHOD AND APPARATUS FOR CALIBRATING A MICROKERATOME

[75] Inventors: Raymond C. Clark, Caputa; Hilton L. Grisel, Sturgis; Kent D. Reimann, Rapid City, all of S. Dak.

[73] Assignee: Chiron Vision Corporation, Irvine, Calif.

[21] Appl. No.: 190,515

[22] Filed: Feb. 2, 1994

[51] Int. Cl.$^6$ .............................. A61B 19/00; A61F 9/00
[52] U.S. Cl. ............................................ 606/130; 606/166
[58] Field of Search ........................... 128/898; 606/130, 606/166, 167; 30/346, 350

[56] References Cited

U.S. PATENT DOCUMENTS

| | | |
|---|---|---|
| 679,779 | 8/1901 | Pierpont . |
| 936,667 | 10/1909 | Reynolds . |
| 1,761,260 | 6/1930 | Gallasch . |
| 1,896,828 | 2/1933 | Nichterlein . |
| 1,974,606 | 9/1934 | Fassin . |
| 2,486,645 | 11/1949 | Hager . |
| 2,539,597 | 1/1951 | Staples . |
| 2,648,138 | 8/1953 | Gase . |
| 2,697,433 | 12/1954 | Zehnder ................................. 606/130 |

(List continued on next page.)

FOREIGN PATENT DOCUMENTS

| | | |
|---|---|---|
| 0531756A2 | 8/1992 | European Pat. Off. . |
| 1657180A1 | 6/1991 | U.S.S.R. . |
| 2092008 | 8/1982 | United Kingdom . |
| 2095119 | 9/1982 | United Kingdom . |
| 2129957 | 5/1984 | United Kingdom . |
| 2179859 | 3/1987 | United Kingdom . |
| WO87/05799 | 10/1987 | WIPO . |
| WO93/06783 | 4/1993 | WIPO . |

OTHER PUBLICATIONS

"The Optical Micrometer", by R. V. Jones, May–Jun. 1976, vol. 15, No. 3, Optical Engineering, pp. 247–250.
"A New Keratome", by Robert C. Drews, M. D., Mar.–Apr. 1967, 71(2), Trans American Academy of Ophthalmology and Otolaryngology, p. 366.
"Disposable Keratome Blade and Its Use in Cataract Surgery", by J. Elliott Blaydes, Jr., M. D., Nov. 1971, 72(5), American Journal of Ophthalmology, p. 1012.
"New Methods in Refractive Corneal Surgery—An Experimental Study", by J. Draeger et al., May 1988, 192(5) Klin. Mbl. Augenheilk, pp. 458–461.
"A Semi-Automatic Electric Keratome for Lamellar Corneal Graft", by J. Draeger, Sep. 1975, 167(3), Klin. Mbl. Augenheilk, pp. 353–359.
"Instrumentation for Lamellar Refractive Surgery", ©1988, 1989, Bores Eye Institute, Chapter 4, pp. 1–9.
"An Independent Evaluation of Second Generation Suction Microkeratomes," by Robert F. Hofmann, M. D., and Samir J. Bechara, M. D., Refractive & Corneal Surgery, vol. 8, Sep./Oct. 1992, pp. 348–354.
"SCMD Keratome Unit," by G. Richard Smith, Refractive & Corneal Surgery, vol. 6, May/Jun. 1990, p. 207.

*Primary Examiner*—Michael Powell Buiz
*Assistant Examiner*—Nancy Mulcare
*Attorney, Agent, or Firm*—Banner & Allegretti, Ltd.

[57] ABSTRACT

An apparatus for calibrating the blade extension of a microkeratome includes a magnifying device and a fixture for holding the microkeratome assembly adjacent thereto. The magnifying device defines a line of sight and includes a reticle visible in the line of sight. The fixture supports the bottom surface of the shim of the microkeratome in a plane parallel to the line of sight of the magnifying device. In measuring the blade extension, the reticle is first aligned with either the cutting edge of the blade or the bottom surface of the gauge member. Relative movement between the reticle and the fixture is effected until the reticle is aligned with the other of the cutting edge and bottom surface of the gauge member. A measuring device monitors the relative movement. The reading of the measuring device equals the blade extension of the microkeratome.

15 Claims, 11 Drawing Sheets

U.S. PATENT DOCUMENTS

| | | |
|---|---|---|
| 3,167,868 | 2/1965 | Arneson . |
| 3,217,416 | 11/1965 | Bachert et al. . |
| 3,231,982 | 2/1966 | Ribich . |
| 3,331,650 | 7/1967 | Williams . |
| 3,508,835 | 4/1970 | Ware . |
| 3,535,793 | 10/1970 | Williams et al. . |
| 3,583,403 | 6/1971 | Pohl et al. . |
| 3,606,550 | 9/1971 | Proksa . |
| 3,701,199 | 10/1972 | Lewis . |
| 3,846,008 | 11/1974 | Sobajima et al. . |
| 4,180,075 | 12/1979 | Marinoff . |
| 4,205,682 | 6/1980 | Crock et al. . |
| 4,265,023 | 5/1981 | Frost et al. . |
| 4,271,740 | 6/1981 | Yamazaki et al. . |
| 4,329,785 | 5/1982 | Peterson . |
| 4,414,749 | 11/1983 | Johannsmeier . |
| 4,438,567 | 3/1984 | Raiha . |
| 4,495,701 | 1/1985 | Nakadoi . |
| 4,499,898 | 2/1985 | Knepshield et al. . |
| 4,526,171 | 7/1985 | Schachar . |
| 4,538,356 | 9/1985 | Knepshield et al. . |
| 4,619,259 | 10/1986 | Graybill et al. . |
| 4,630,378 | 12/1986 | Kulp et al. . |
| 4,660,556 | 4/1987 | Swinger et al. . |
| 4,662,075 | 5/1987 | Mastel et al. . |
| 4,662,370 | 5/1987 | Hoffmann et al. . |
| 4,750,489 | 6/1988 | Berkman et al. . |
| 4,750,491 | 6/1988 | Kaufman et al. . |
| 4,807,623 | 2/1989 | Lieberman . |
| 4,815,218 | 3/1989 | Gordy . |
| 4,884,570 | 12/1989 | Krumeich et al. . |
| 4,898,170 | 2/1990 | Hofmann et al. . |
| 4,903,695 | 2/1990 | Warner et al. . |
| 4,997,437 | 3/1991 | Grieshaber . |
| 5,105,545 | 4/1992 | Fletcher . |
| 5,108,412 | 4/1992 | Krumeich et al. . |
| 5,133,726 | 7/1992 | Ruiz et al. . |
| 5,152,786 | 10/1992 | Hanna . |
| 5,203,865 | 4/1993 | Siepser . |
| 5,215,104 | 6/1993 | Steinert . |
| 5,222,967 | 6/1993 | Casebeer et al. . |
| 5,224,950 | 7/1993 | Prywes . |
| 5,288,292 | 2/1994 | Giraud et al. . |
| 5,447,517 | 9/1995 | Steen et al. ............................ 606/167 |

MICROKERATOME AND METHOD AND APPARATUS FOR CALIBRATING A MICROKERATOME

FIELD OF THE INVENTION

The present invention pertains to a microkeratome, and to a method and apparatus for calibrating the extension of a microkeratome blade.

BACKGROUND OF THE INVENTION

A microkeratome is a surgical implement for performing lamellar refractive surgery, and in particular lamellar keratectomy. This procedure involves the resection of an outer layer of the patient's cornea. As can be appreciated, the depth of the resection must be carefully controlled to ensure a successful operation.

Figure 27:
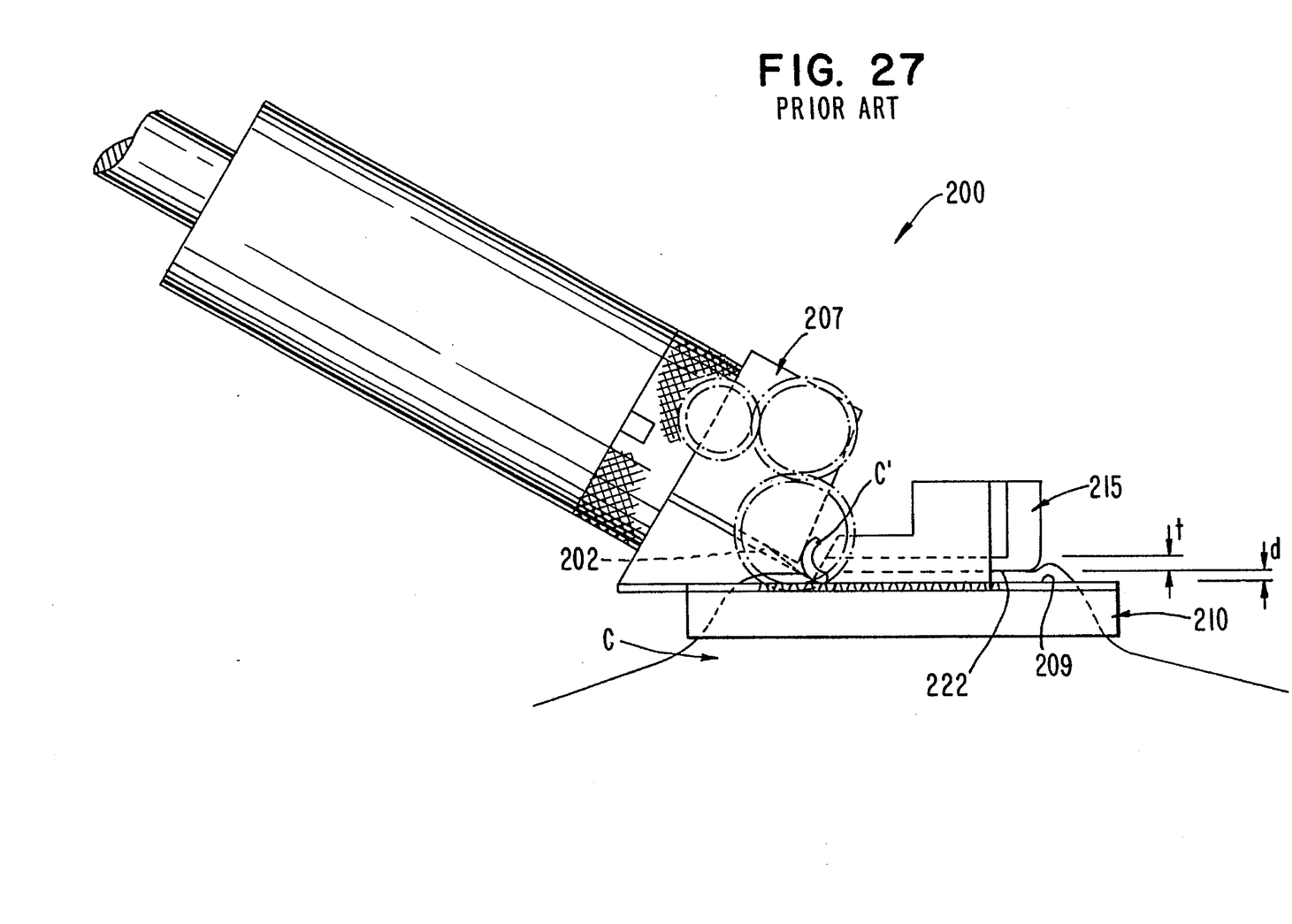
FIG. 27 is a cross sectional view of a prior art microkeratome.

A microkeratome 200 as disclosed, for example, in U.S. Pat. No. 5,133,726 to Ruiz et al. includes a blade 202 to remove an outer layer c' of the cornea C (FIG. 27). Blade 202 is held by a skate 207 which is slidably attached to the top 209 of a ring 210 by a pair of dovetail runners 212. The ring 210 is set over the cornea such that an outer portion of the cornea extends upward above the ring. A shim member 215 is releasably received in a slot 217 along a bottom portion of the skate to engage the cornea. The thickness t of shim 215 sets the vertical distance d between the cutting edge 220 of blade 202 and the bottom surface 222 of shim 215, which in turn, sets the depth of the resection. Shims having different thicknesses can alternatively be received in slot 217 to vary the depth of the cut.

While the components of the microkeratome are fabricated according to precise manufacturing techniques, a surgeon needs to ascertain with certainty the actual depth of the cut which will be effected with a particular shim. Surgeons have not, heretofore, been able to consistently and accurately measure the blade extension; and therefore have been forced to rely solely upon the manufacturer's calibration of the shims.

Further, the use of replaceable shims enables only a finite adjustment of the blade extension. As a result, the options available to the surgeon for a prospective operation are limited. Also, the need for multiple alternative shims requires the manufacture of a number of additional parts—many of which are unused in any one operation. As can be appreciated, this manufacture of alternatively used parts increases the costs of making the microkeratome.

SUMMARY OF THE INVENTION

The present invention is directed to an adjustable microkeratome, and a method and apparatus for setting or measuring the blade extension of a microkeratome.

A microkeratome of the present invention includes a movable foot for engaging the exterior of the cornea. The foot is movable in a vertical direction to alter the distance the cutting edge of the blade extends beyond the bottom surface of the foot. This enables the surgeon to effect resection of the cornea at different desired depths. In the preferred construction, a differential screw mechanism is used to provide infinite adjustment capabilities for the foot.

Also in accordance with the present invention, the extension of a microkeratome blade beyond its adjacent gauge member can be consistently and accurately measured, irrespective of whether the gauge member is a replaceable shim or an adjustable foot. To this end, a microkeratome assembly is supported adjacent to a magnifying device. The magnifying device defines a line of sight and includes a reticle which is visible in the line of sight. The microkeratome assembly is positioned so that the bottom surface of the gauge member lies in a plane parallel to the line of sight. The reticle is first aligned with either the cutting edge of the blade or the bottom surface of the gauge member. Thereafter, relative movement is effected between the reticle and the microkeratome assembly so that the reticle is next aligned with the other of the cutting edge of the blade or bottom surface of the gauge member. The relative movement is monitored by a measuring device. The reading of the measuring device equals the distance between the cutting edge and the bottom surface of the gauge member, which in turn, equals the extension of the blade.

According to another aspect of the invention, the blade extension of a microkeratome having infinite adjustment capability can be accurately set. To set the blade extension, a microkeratome assembly is supported adjacent a magnifying device so that the bottom surface of the foot lies in a plane parallel with the line of sight of the magnifying device. Once the assembly is properly mounted, the cutting edge of the blade is aligned with the reticle of the magnifying device. Relative movement, monitored by a measuring device, is then effected between the reticle and the cutting edge. The relative movement is continued until the distance between the reticle and the cutting edge equals the desired extension of the blade. The foot of the microkeratome assembly is then adjusted so that the bottom surface of the foot is aligned with the reticle.

In the preferred construction, an apparatus for calibrating a microkeratome includes a fixture for holding the microkeratome assembly within the line of sight of the magnifying device. The fixture has jaws which engage and hold the runners of the microkeratome assembly parallel to the line of sight. This arrangement ensures that the bottom surface of the gauge member (i.e. the shim or foot) is oriented parallel to the line of sight. The jaws of the fixture define a three point mount for supporting and accurately setting the microkeratome assembly for the desired measurement. The jaws of the fixture are further constructed to permit a quick mount and release of the microkeratome assembly, and to permit adequate lighting for visible observation of the blade and shim components.

DETAILED DESCRIPTION OF THE PREFERRED EMBODIMENTS

One aspect of the present invention relates to a microkeratome 11 (FIGS. 23–26). Microkeratome 11 preferably has much of the same construction as the microkeratome of U.S. Pat. No. 5,133,726, which is incorporated by reference for the common structure and operation of the microkeratome not discussed in this application.

Microkeratome 11 includes a skate 12 provided with an upper section 12a and a lower section 12b. Upper section 12a includes a body 13 and a threaded segment 15a. Lower section 12b includes a pair of runners 17a, 17b, a threaded segment 15b, and a bridge structure 40. Sections 12a, 12b are matingly fit together so that segments 15a, 15b form a threaded rod on which is received a lock nut 25.

Skate body 13 includes an opening 21 adapted to movably receive therein a blade holder (not shown) attached to cutting blade 27. The blade holder is coupled to an eccentric (not shown) extending from a motor encased in handle 31 to laterally reciprocate the blade during the operation. Longitudinal bore 23 and transverse bore 35 are adapted to receive therein an endless pinion and a pinion-shaft respectively. The endless pinion and pinion-shaft cooperate to drive skate 12 across the base ring 39 as set forth in the '726 patent. Runners 12a, 12b slidably engage tracks 37 on ring 39 to guide skate 12 and blade 27 across the cornea. Preferably, runner 17a has a rectangular slot and runner 17b has a dovetail shape. The use of the rectangular slot alleviates binding which can occur with two dovetail runners and prevents improper positioning of the skate on the ring. Nonetheless, both runners may be dovetail shaped if desired.

Figure 25:
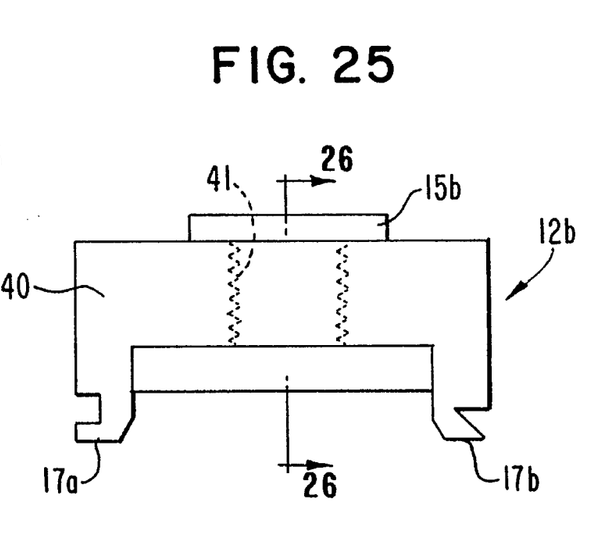
FIG. 25 is a front view of a portion of a skate according to the present invention.
Figure 26:
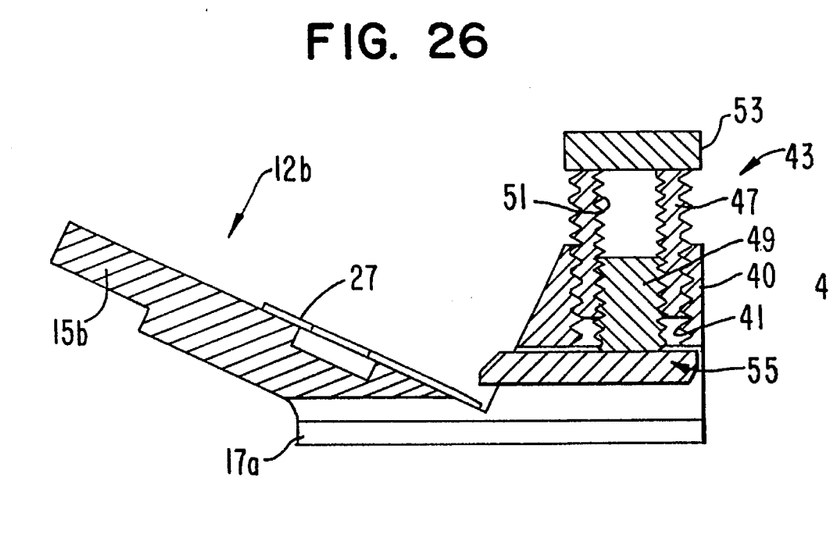
FIG. 26 is a cross sectional view taken along line 26—26 in FIG. 25, with the cutting blade, differential screw mechanism, and foot included.

Bridge 40 defines a threaded central bore 41 into which is matingly received a differential screw mechanism 43. Screw mechanism 43 includes an outer, annular screw 47 provided with an axial bore 51 and an inner screw 49. Annular screw 47 is provided with inner and outer threads. The outer threads of screw 47 mate with the threads in bore 41. The inner threads along bore 51 mate with the threads of inner screw 49. As is well known with differential screws, the pitches of the different threads are selected so that substantial turning of outer screw 47 causes inner screw 49 to move axially only a small amount. The upper end of outer screw 47 is provided with a knurled handle 53 or other means to effect rotation of the screw.

Figure 23:
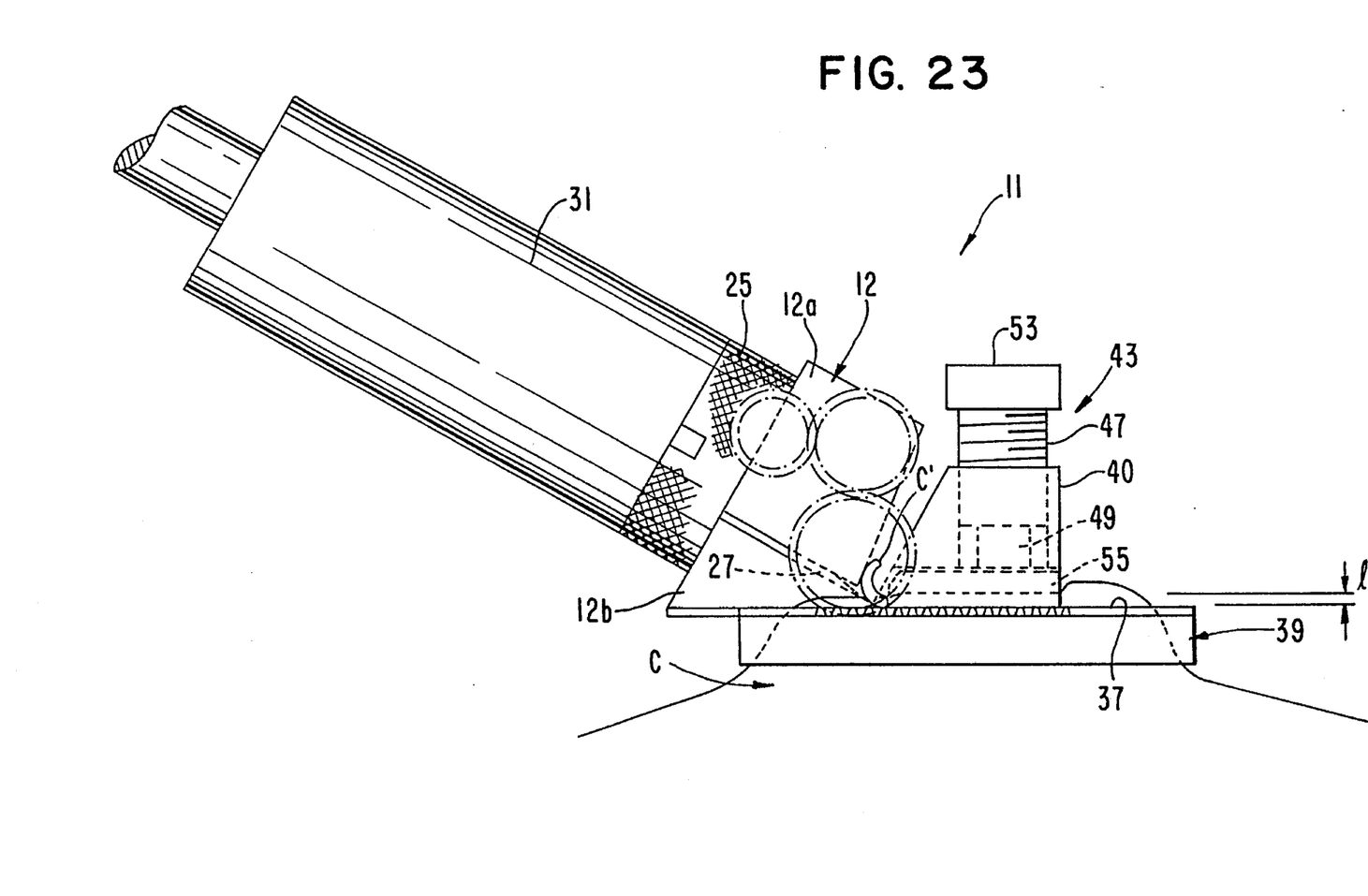
FIG. 23 is a side view of a microkeratome according to the present invention.
Figure 24:
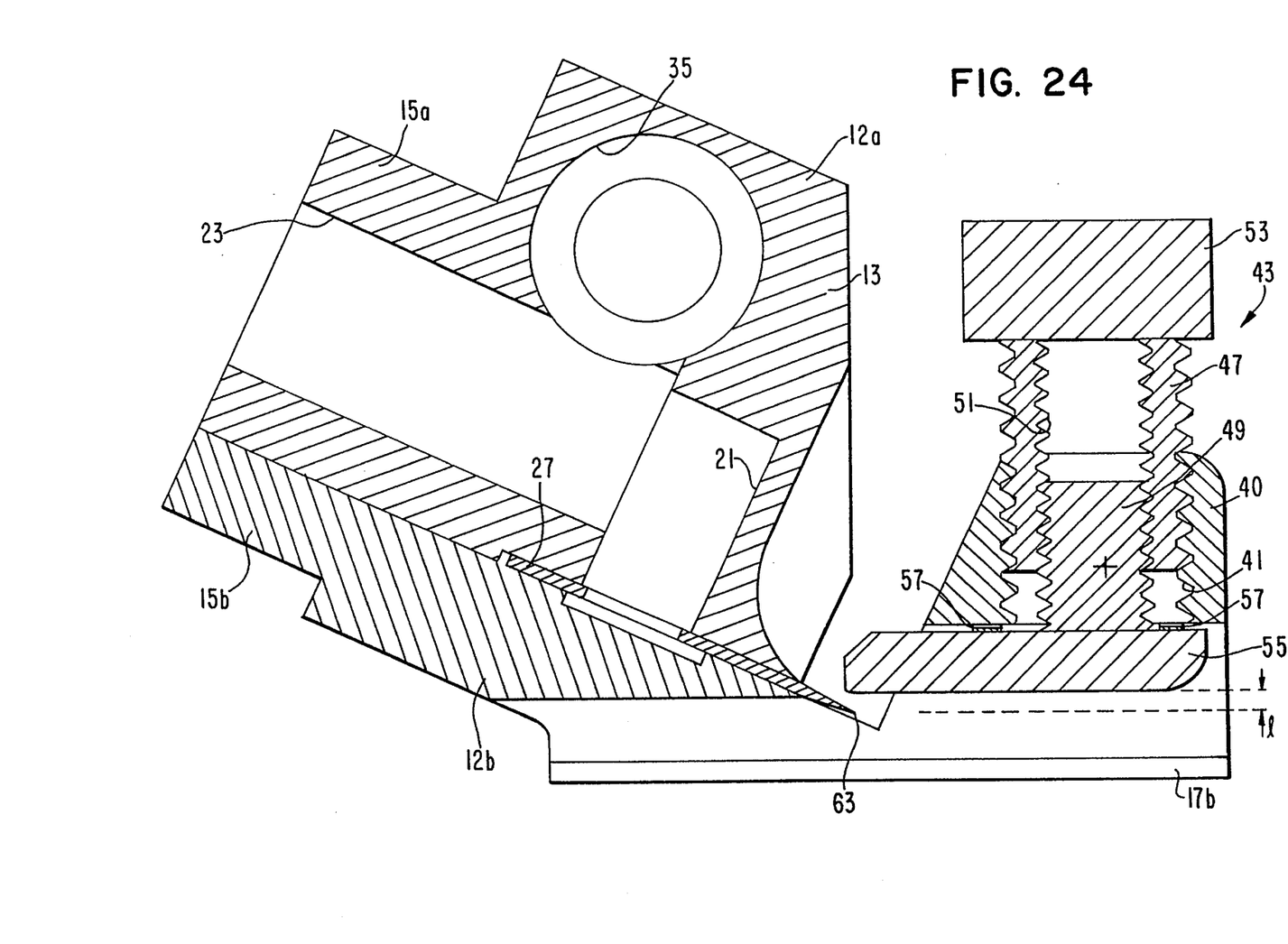
FIG. 24 is an enlarged cross sectional view of a microkeratome assembly in accordance with the present invention.

A foot 55 is fixedly attached to the lower end of screw 49. Foot 55 defines a pair of side walls 59 and a bottom surface 61. Side walls 59 are lightly abutted against opposing inner walls 62 to prevent rotation of the foot during actuation of differential screw mechanism 43. A pair of leaf springs 57 are preferably positioned between the foot and the skate to alleviate the effects of backlash in connection with screw mechanism 43. Bottom surface 61 of foot 55 is adapted to engage the outer surface of the cornea and set the depth of the resection in cooperation with blade 27. As best seen in FIGS. 23 and 24, the vertical distance l between bottom surface 61 of foot 55 and cutting edge 63 of blade 27 is the blade extension of the microkeratome, or in other words, the depth of the resection to be made during the operation.

Figure 1:
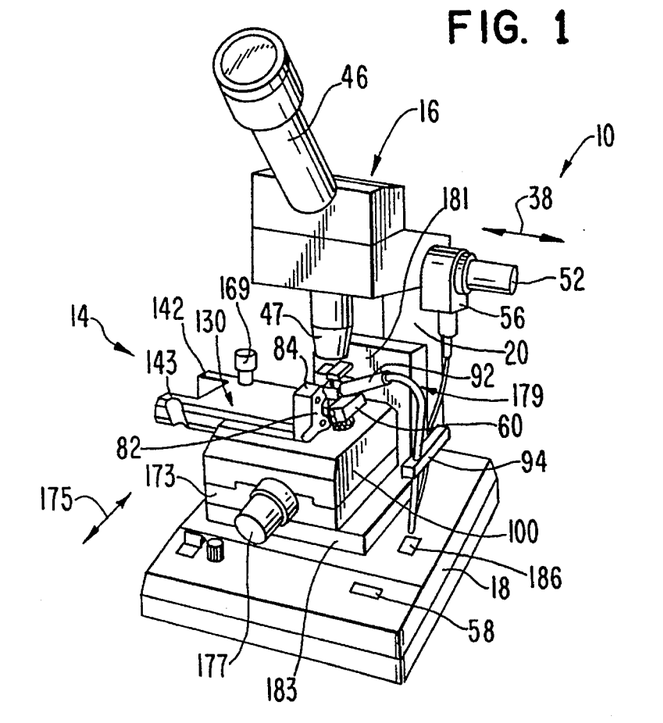
FIG. 1 is a perspective view of the present invention.

Another aspect of the present invention relates to a method and apparatus 10 for calibrating (i.e., measuring or setting) the blade extension of a microkeratome. In the preferred construction, apparatus 10 includes a fixture 14 for holding a microkeratome assembly and a magnifying device 16 for viewing the relevant components of the microkeratome (FIG. 1). For purposes of illustration, the microkeratome is shown generally as structured in U.S. Pat. No. 5,133,726. Of course, microkeratomes of other constructions, including microkeratome 11 discussed above, could be used with this aspect of the present invention.

Figure 2:
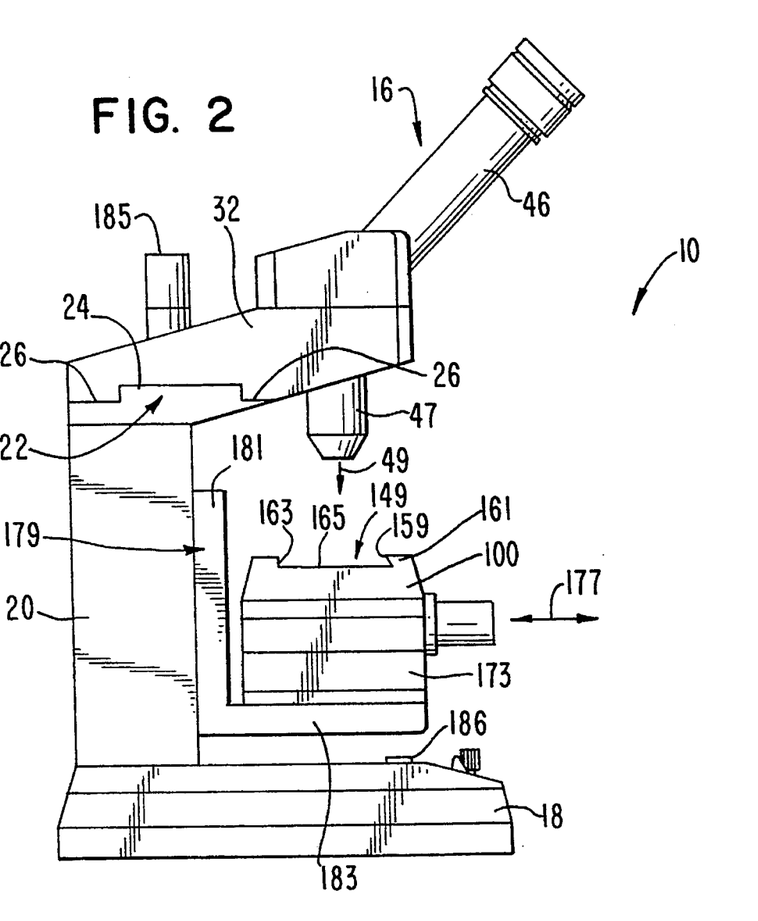
FIG. 2 is a side elevational view thereof.
Figure 3:
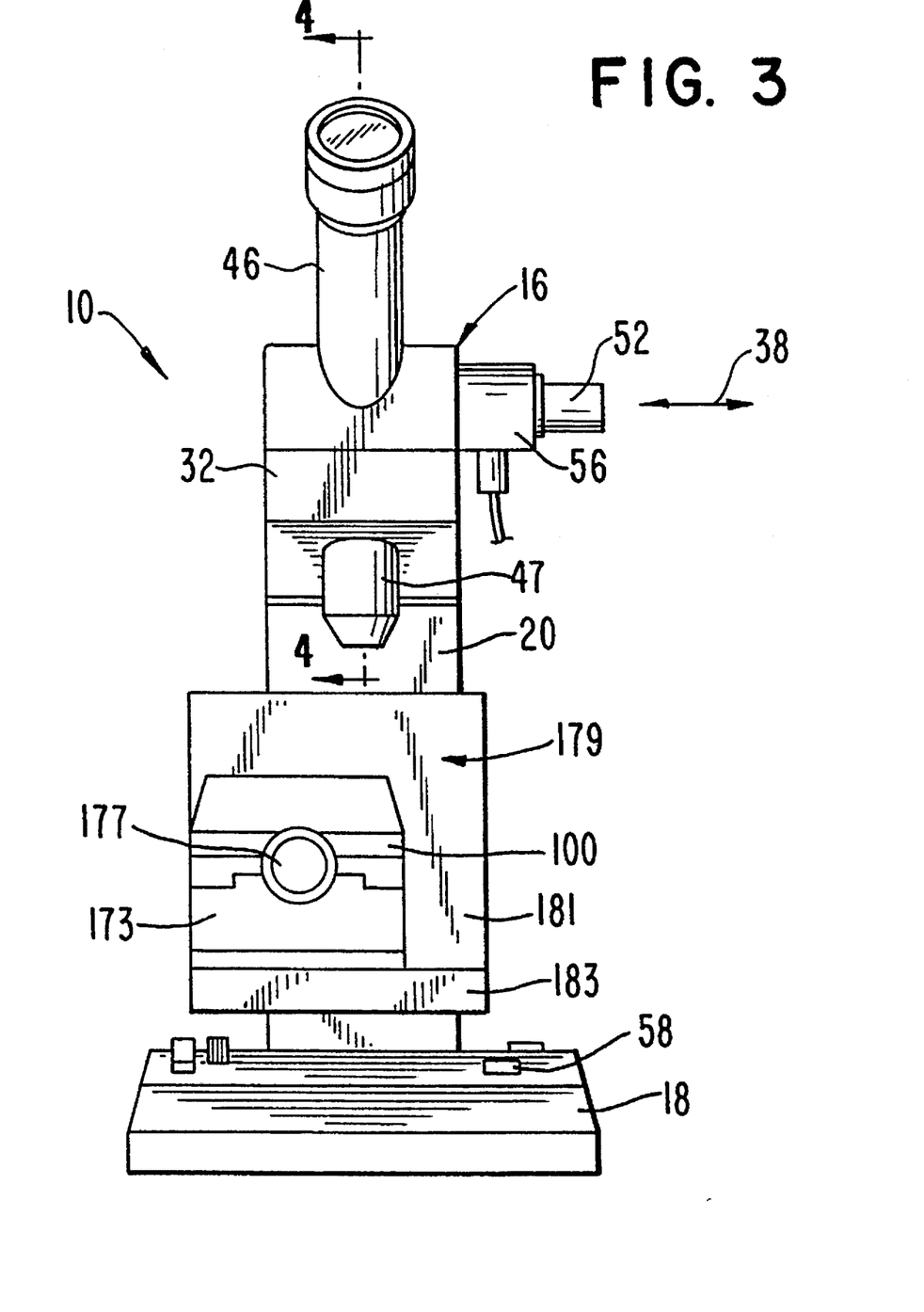
FIG. 3 is a front elevational view thereof.
Figure 4:
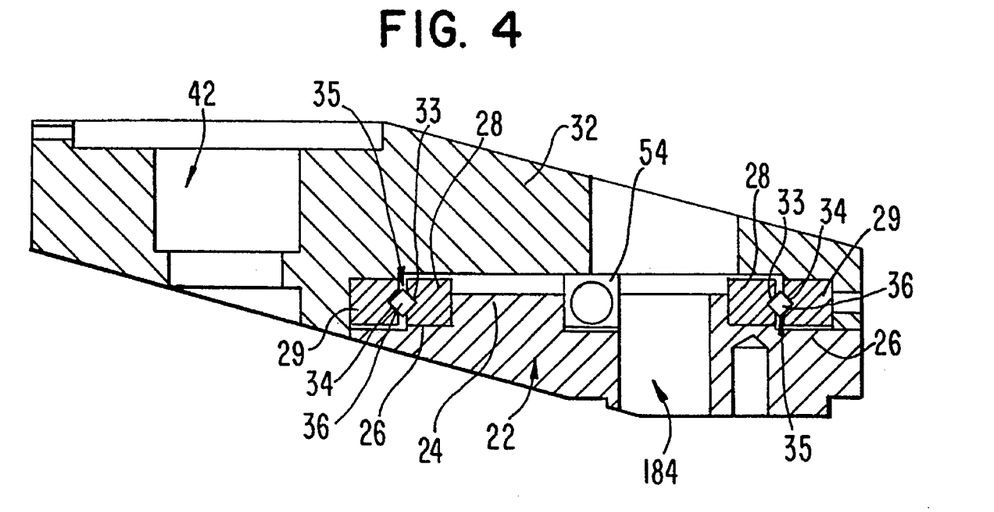
FIG. 4 is a cross sectional view taken along line 4—4 in FIG. 3, with the ocular components and post adjustment assembly omitted.

Apparatus 10 is further comprised of a relatively broad base 18 and an upstanding post 20 (FIGS. 1–3). Magnifying device 16 is adjustably mounted to the top of the post for movement along the X-axis. To accommodate the desired movement, the top of the post is configured to define a rail 22 which extends along the X-axis (FIGS. 2 and 4). Rail 22 has a central head 24 and a pair of shoulders 26. A carriage 32 having a complementarily shaped base portion is movably mounted on the rail. Bearing guides 28, 29 are fixedly secured to shoulders 26 and carriage 32, respectively (FIG. 4). Guides 28, 29 each defines a V-shaped groove 33, 34 along one side. Grooves 33, 34 are placed in opposed relation to one another, to form a pair of channels 35. Cylindrical bearings 36 are placed in channels 35 in an alternating arrangement, such that each bearing is oriented ninety degrees relative to its adjacent bearings. This bearing structure ensures that carriage 32 moves in only the X-axis direction as indicated by arrows 38 (FIGS. 1 and 3).

Figure 21:
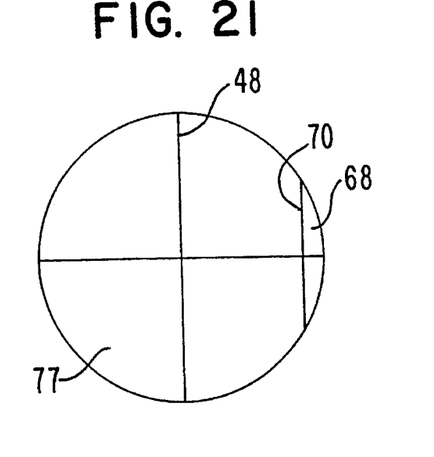
FIG. 21 is a view as seen through the magnifying device of the present invention.
Figure 22:
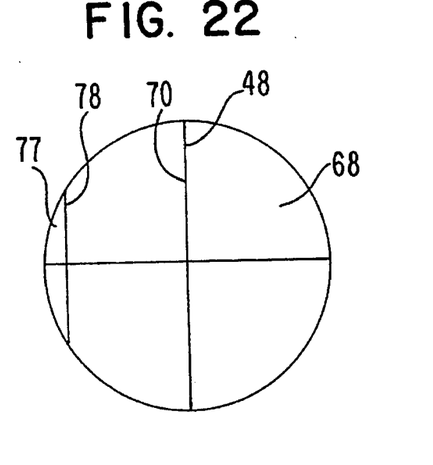
FIG. 22 is a second view as seen through the magnifying device of the present invention.

Carriage 32 extends forward from rail 22 in a cantilevered manner to support the optical assembly of magnifying device 16 over fixture 14 (FIGS. 1, 2 and 4). The magnifying device includes a magnifying lens within barrel 47 and an eyepiece 46 (FIGS. 1–3). Barrel 47 defines a circular range of vision which is seen through eyepiece 46 (FIGS. 21–22). The outward longitudinal extension of this circular range from barrel 47 defines the line of sight for the magnifying device, as indicated by arrow 49 (FIG. 2). Eyepiece 46 includes a reticle which defines a linear marking, preferably in the form of a cross hair 48 (FIGS. 21–22).

Carriage 32 is linearly moved in the X-axis direction by preferably a screw mechanism 52 (FIGS. 1 and 3). Screw mechanism 52 is comprised of a screw threadedly received through nut 54 fixed to carriage 32 (FIG. 4). As the screw is turned, the carriage is moved linearly along rail 22. A digital encoder 56 is used to measure the amount of movement caused by turning the screw (FIGS. 1 and 3). Of course a micrometer or other measuring device could also be used. A digital display 58 located in base 18 is provided to indicate the distance traveled by the carriage (FIGS. 1 and 3).

Figure 5:
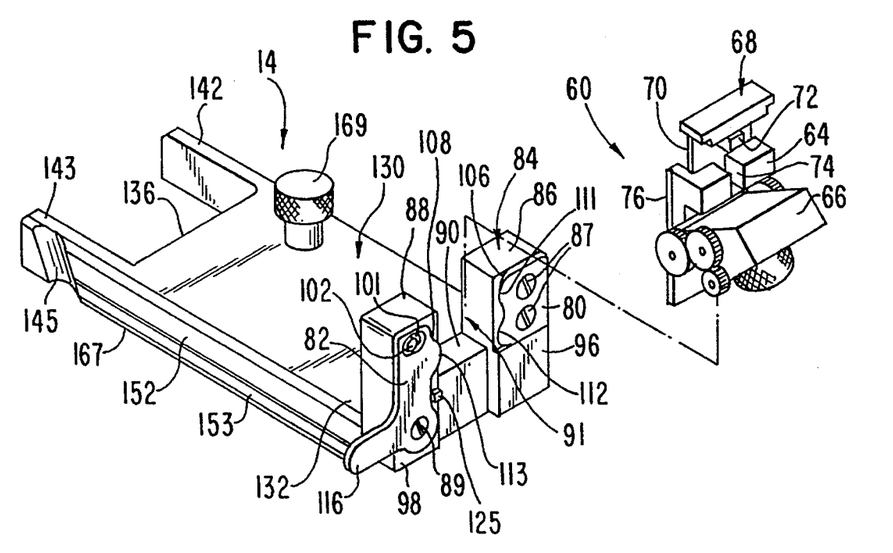
FIG. 5 is a perspective view of a fixture of the present invention and a microkeratome.

To facilitate measurement of the blade extension, the handle and ring components of the microkeratome are removed. For purposes of illustration, a microkeratome assembly in accordance with the prior art is shown mounted in fixture 14 (FIGS. 1 and 5). Nevertheless, a microkeratome 11 with infinite adjustment capabilities could be mounted in the fixture in the same way. In any event, the remaining assembly 60 includes a skate 64, a blade holding unit 66 and a shim 68 (FIGS. 1 and 5). In FIG. 5, shim 68 is shown as being partially inserted into skate 64 in order to illustrate its bottom surface 70. In actual use with apparatus 10, the shim would be fully inserted such that tenon 72 would be fully received into mortise 74. Skate 64 includes a pair of parallel dovetail runners 76 adapted to slidably mount the skate to the ring (not shown). Blade holding unit 66 includes a blade holder (not shown) and a blade 77 with a cutting edge 78 (FIGS. 21 and 22).

Figure 9:
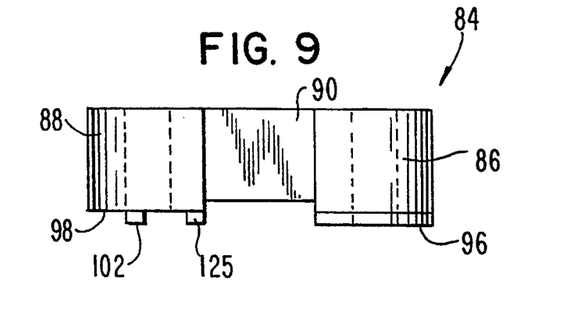
FIG. 9 is a top view of the support element.
Figure 10:
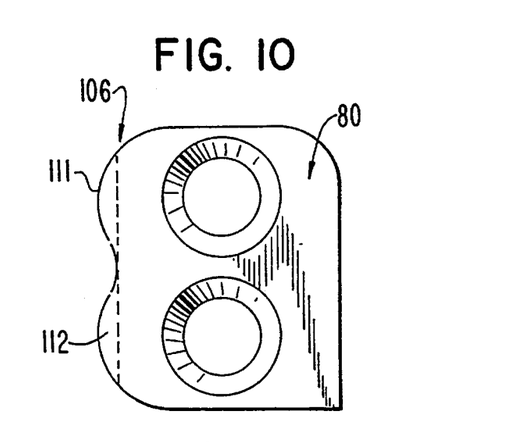
FIG. 10 is a front view of the fixed jaw of the fixture.
Figure 11:
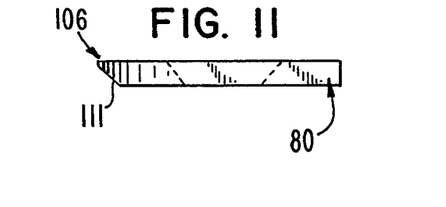
FIG. 11 is a top view of the fixed jaw.

Microkeratome assembly 60 is mounted in fixture 14 for viewing through eyepiece 46 (FIGS. 1 and 5). In particular, skate 64 is engaged by jaws 80, 82 and held so that dovetail runners 76 are positioned parallel to the line of sight. Jaws 80, 82 are attached to a U-shaped support 84 having upstanding legs 86, 88 and a lower bight portion 90 (FIGS. 5–15). The gap 91 defined between legs 86, 88 of support 84 permits a portion of the surrounding light to shine on blade 77 and shim 68. An auxiliary lamp 92, supported by arm 94, is preferably also provided for increased lighting (FIG. 1). Further, bight portion 90 is recessed relative to front faces 96, 98 of legs 86, 88 to permit increased lighting to shine up from the main lamp (not shown) in table 100 (FIGS. 5 and 9).

Figure 6:
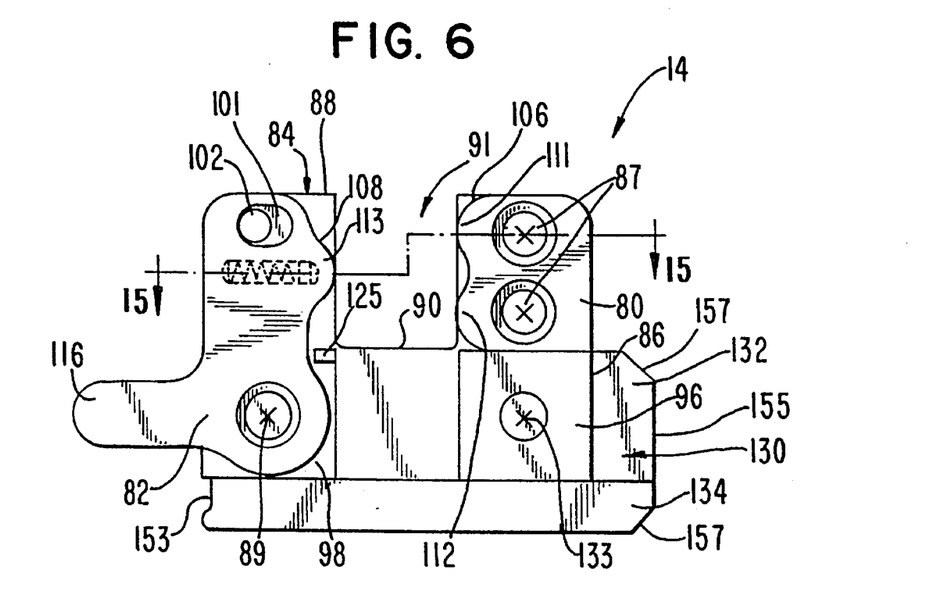
FIG. 6 is a front end view of the fixture.
Figure 7:
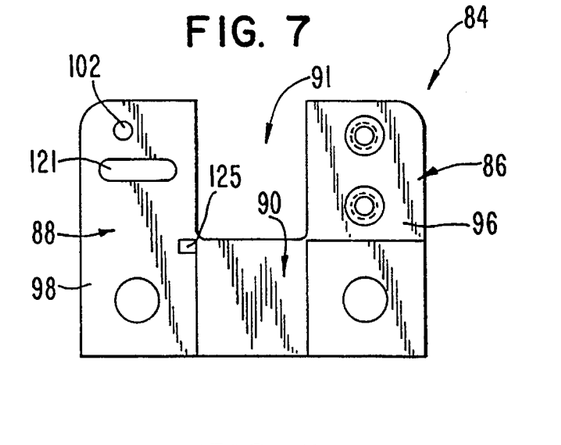
FIG. 7 is a front view of a support element of the fixture.
Figure 8:
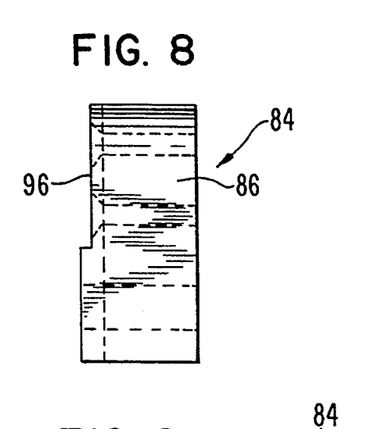
FIG. 8 is a side view of the support element.
Figure 12:
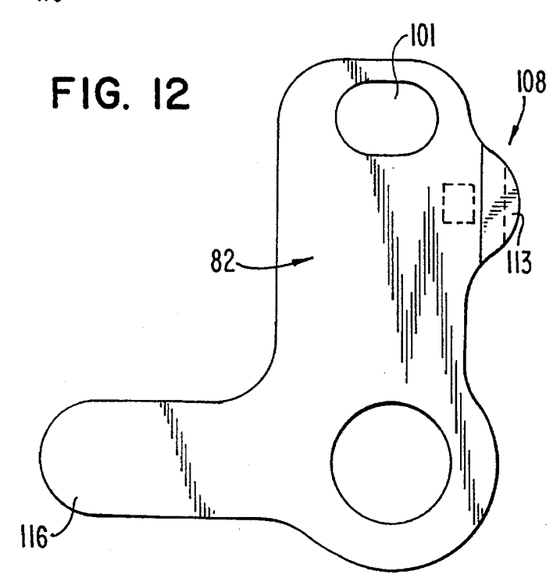
FIG. 12 is a front view of the movable jaw of the fixture.
Figure 13:
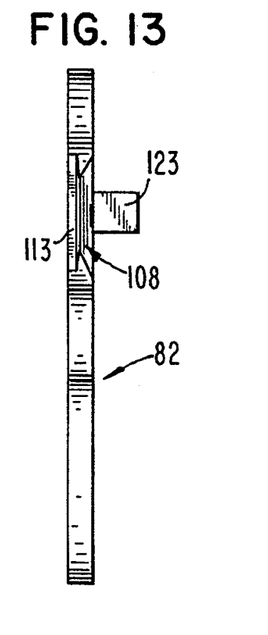
FIG. 13 is a side view of the movable jaw.
Figure 14:
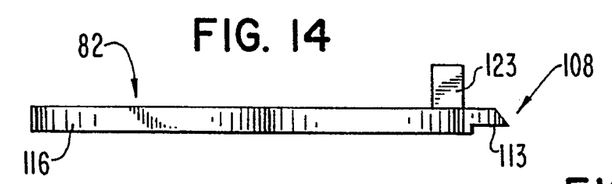
FIG. 14 is a top view of the movable jaw.
Figure 15:
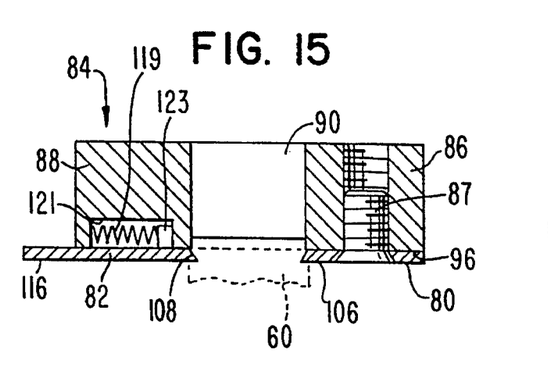
FIG. 15 is a cross sectional view taken along line 15—15 in FIG. 6.
Figure 16:
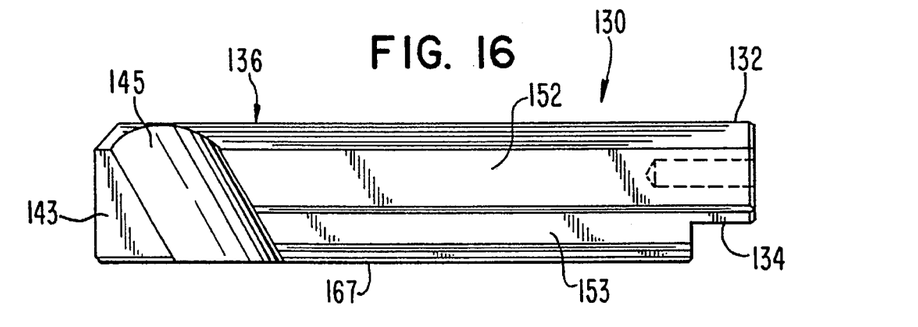
FIG. 16 is the left side elevational view of the tray of the fixture.
Figure 17:
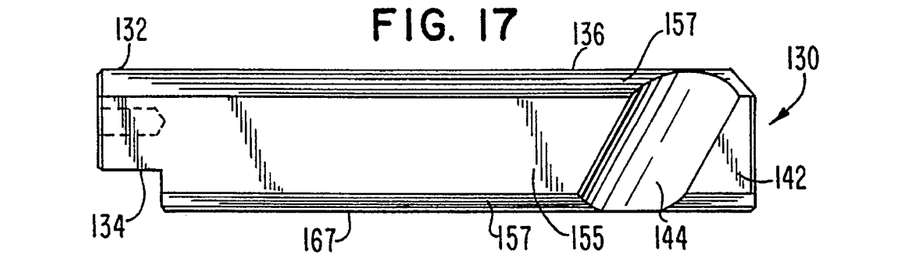
FIG. 17 is the right side elevational view of the tray.
Figure 18:
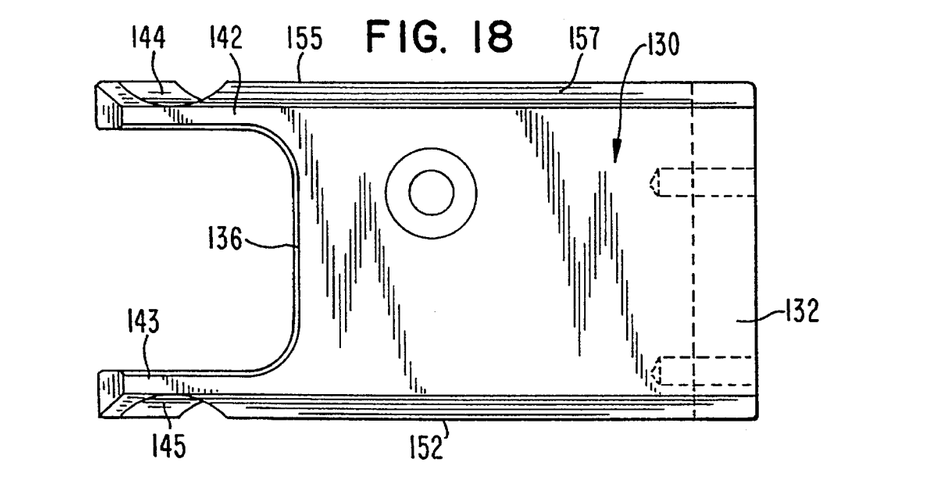
FIG. 18 is a top plan view of the tray.
Figure 19:
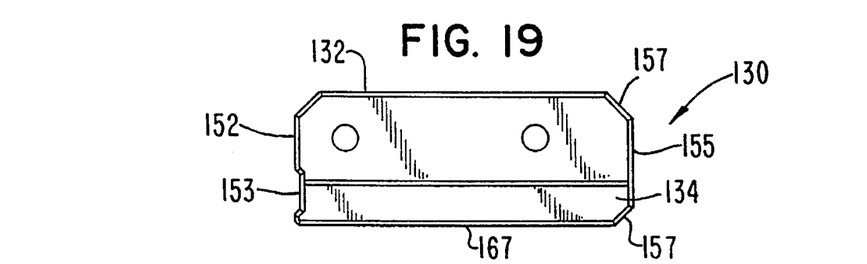
FIG. 19 is a front end view of the tray.

Fixed jaw 80 is secured to leg 86 by a pair of screws 87 (FIGS. 5–11 and 15). Movable jaw 82 is preferably pivotally attached at its bottom end to leg 88 by a screw 89 (FIGS. 5–6 and 12–15). A slot 101, defined in the upper end of jaw 82, is received over a projection 102 to provide support and clearance for the jaw's movement. A spring 119 works to bias jaw 82 into its closed position and thereby supply the gripping force necessary to hold microkeratome assembly 60 (FIGS. 6 and 12–15). In the preferred construction, a cavity 121 is defined in front face 98 of leg 88 to receive a lug 123 extending rearwardly from jaw 82. Spring 119 presses against lug 123 to normally rotate jaw 82 toward fixed jaw 80. A stop 125 projects from face 98 to properly position the microkeratome assembly. A lever 116 extends laterally outward from jaw 82 to facilitate manual pivoting of the jaw (FIGS. 5, 6 and 12).

The movable jaw may also have other constructions. For instance, the movable jaw may be a block member provided with a transverse channel and a gripper member which is mounted for movement towards and away from the fixed jaw. The gripper member would be spring biased towards the fixed jaw, but manually movable in a rearward direction for release of the microkeratome assembly. Of course, other jaw arrangements could also be used.

Jaws 80, 82, along their inner edges 106, 108, are beveled in order to matingly engage dovetail runners 76 of microkeratome assembly 60. The jaws form a three point mount to ensure accurate positioning of assembly 60. Preferably, inner end 106 of jaw 80 has an undulated configuration which defines two spaced contact points 111, 112. Inner end 108 of jaw 82 defines an opposed single contact point 113 located between points 111, 112.

Support 84 is secured to the front end 132 of a relatively flat, elongated tray 130 by a pair of screws 89, 133 (FIGS. 5–6 and 16–19); although other attachment means could be used. Front end 132 is preferably notched at 134 in order to provide ample clearance for positioning of the tray when it is used with certain pre-existing inspection microscopes; that is, to permit proper placement of the microkeratome assembly within the line of sight of the magnifying device. Also, as seen in FIG. 6, tray 130 is wider than support 84 to accommodate the channel defined in certain pre-existing inspection microscopes. The presence of the notch and enlarged width is, of course, not essential to the invention. The rear end 136 of tray 130 is bifurcated into a pair of legs 142, 143 to form a suitable handgrip. Each leg 142, 143 is provided with an angled groove 144, 145 for better manipulation of the fixture. Of course other handles or gripping arrangements could be employed.

Figure 20:
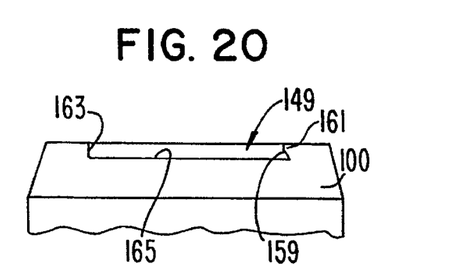
FIG. 20 is a partial side view of the upper portion of the table of the present invention.

Table 100 defines a channel 149 which matingly receives tray 130 (FIGS. 1, 2 and 20). The sides of tray 130 and channel 149 are configured to temporarily hold the tray in place and to enable the tray to be quickly inserted into and removed from the channel (FIGS. 2 and 16–19). Specifically, one side 152 of tray 130 includes a longitudinal groove 153 which is received over a complementary ridge 161 defined on channel side wall 159. The opposite side 155 of tray 130 is formed with chamfered corners 157, but not a groove. The opposite side wall 163 of the channel defines a planar surface set at a right angle to the bottom 165 of the channel.

To insert tray 130 into channel 149, the tray is first inclined at an angle of about 45 degrees with side 152 facing generally downward toward channel 149. Fixture 14 is next moved into the channel so that groove 153 is partially received over ridge 161. Fixture 14 is then rotated until bottom 167 of tray 130 lies against bottom 165 of channel 149. Chamfered corners 157 provide the clearance necessary to effect the rotation of the tray into and out of the channel. The tray is securely held in place for measurement of the blade extension by a bolt 169 received into a threaded bore (not shown) defined in the bottom 165 of channel 149. Of course, fixture 14 could be secured into channel 149 in other ways.

Table 100 is movably supported on block 173 (FIGS. 1–3) with the same bearing construction as described above for rail 22 and carriage 32. The bearing construction (not shown) connecting table 100 to block 173, however, is orthogonal to the orientation of bearing guides 28, 29. In this way, table 100 is restricted to movement only along the Y-axis, as indicated by arrows 175 (FIGS. 1–2). A screw mechanism 177 effects the movement of the table along block 173 (FIGS. 1–3). Such movement of the table is used to bring microkeratome assembly 60 into the line of sight for magnifying device 16 and to facilitate inspection of the entire cutting edge 78 for damage.

Block 173 is fixedly attached to a bracket 179 which is movably connected to post 20 (FIGS. 1–3). Bracket 179 includes a mounting leg 181 which lies against post 20 and a support leg 183 which projects outward over base 18. Support leg 183 supports block 173 underneath magnifying device 16 to enable viewing of microkeratome assembly 60. Mounting leg 181 is coupled to a screw adjustment mechanism 185 positioned within post 20. Screw adjustment mechanism 185 extends through passage 184 defined in rail 22, carriage 32 and post 20. The screw adjustment mechanism moves bracket 179 vertically along post 20 to enable focusing of magnifying device 16.

The blade extension of a microkeratome is measured by first placing assembly 60 into jaws 80, 82 so that cutting edge 78 faces upward toward magnifying device 16. Preferably, fixture 14 is already mounted onto table 100 when microkeratome assembly 60 is attached, but it could be mounted afterward. If necessary, screw adjustment mechanism 177 is turned to place assembly 60 within the line of sight for magnifying device 16. Screw mechanism 52 is adjusted so that cross hair 48 is aligned with the cutting edge 78 of blade 77 (FIG. 21). Encoder 56 is then zeroed by pushing button 86. Screw mechanism 52 is again rotated so that magnifying device 16 is moved along the X-axis until cross hair 48 is aligned with the bottom 70 of shim 68 (FIG. 22). Alternatively, cross hair 48 can be first aligned with bottom surface 70 of shim 68 and then moved to cutting edge 78. In the case with microkeratome 11, the reticle is successively aligned with the cutting edge of the blade and the bottom surface of the foot, or vice versa. In any event, the reading in display 58 is the distance the blade extends beyond the bottom surface of the gauge member 55 or 68.

Apparatus 10 can also be used to accurately set the blade extension of microkeratome 11. In this process, handle 31 and ring 39 of microkeratome 11 are removed to form a microkeratome assembly 11'. Assembly 11' is mounted to fixture 14 with the runners 17a, 17b of skate 12 engaged by jaws 80, 82. The beveled jaw is able to securely hold runner 17a by engaging the corner of the rectangular slot. As with measuring the blade extension, the bottom surface 61 of foot 55 is held vertically in a plane parallel with the line of sight of magnifying device 16. Additionally, blade 27 is oriented such that cutting edge 63 faces upwardly. Although fixture 14 is preferably mounted to table 100 before assembly 11' is attached, the fixture may be so mounted after the attachment of assembly 11'.

Once fixture 14 with assembly 11' is properly mounted to table 100, screw mechanism 177 is adjusted, if necessary, to bring assembly 11' within the line of sight of magnifying device 16. Screw mechanism 52 is next adjusted so that cross hair 48 is aligned with the cutting edge 63 of blade 27. At this juncture, encoder 56 is zeroed. Using encoder 56 and screw mechanism 52, carriage 32 is adjusted so that cross hair 48 is moved away from the cutting edge of blade 27 a distance equal to the desired extension of the blade. Thereafter, differential screw mechanism 43 is actuated so as to adjust the position of foot 55. The movement of foot 55 is continued until its bottom surface 61 is aligned with cross hair 48. The foot and blade now define the desired cutting depth for the operation.

The above discussion concerns the preferred embodiments of the present invention. Nevertheless, as can be appreciated, apparatus 10 can be constructed in a number of different ways without departing from the present invention. For instance, the X and Y axis adjustments could be reversed such that the fixture is moved along the X-axis and the carriage along the Y-axis. In addition, the adjustments could be accomplished solely by moving either the fixture or the carriage in both directions. Also, the line of sight could be arranged horizontally instead of vertically. Further changes and alterations may also be made without departing from the spirit and broader aspects of the invention as defined in the claims.

We claim:

1. A method for measuring the blade extension of a microkeratome assembly having a blade defining a cutting edge and a gauge member defining a bottom surface spaced from the cutting edge, said method comprising:

positioning the microkeratome assembly adjacent a magnifying device defining a line of sight for the user and including a reticle visible in the line of sight, said reticle defining a linear marking, said microkeratome assembly being positioned within the line of sight such that the bottom surface of the gauge member lies in a plane parallel to the line of sight;

aligning the linear marking with one of the cutting edge or the bottom surface of the gauge member;

causing relative movement between the reticle and the microkeratome assembly in a direction perpendicular to the linear marking so that the linear marking is aligned with the other of the cutting edge or the bottom surface of the gauge member;

monitoring the relative movement with a measuring device; and reading the amount of movement recorded by the measuring device to obtain the blade extension.

2. A method in accordance with claim 1 in which said causing of the relative movement includes moving the magnifying device in a direction perpendicular to the linear marking.

3. A method in accordance with claim 2 in which said moving of said magnifying device is effected by a screw mechanism.

4. A method in accordance with claim 1 in which said monitoring of the relative movement is effected by an encoder.

5. A method in accordance with claim 1 in which said causing of the relative movement includes moving the microkeratome assembly in a direction perpendicular to the linear marking.

6. A method in accordance with claim 1 in which said causing and measuring of the relative movement is effected by a micrometer.

7. A method in accordance with claim 1 in which said gauge member is a replaceable shim.

8. A method in accordance with claim 1 in which said gauge member is an adjustable foot.

9. A method for setting the blade extension of a microkeratome assembly having a blade defining a cutting edge and an adjustable foot defining a bottom surface spaced from the cutting edge, said method comprising:

positioning the microkeratome assembly adjacent a magnifying device defining a line of sight for the user and including a reticle visible in the line of sight, said reticle defining a linear marking, said microkeratome assembly being positioned within the line of sight such that the bottom surface of the foot lies in a plane parallel to the line of sight;

aligning the linear marking with the cutting edge of the blade;

causing relative movement between the reticle and the microkeratome assembly in a direction perpendicular to the linear marking until said linear marking is spaced from the cutting edge of the blade a distance equal to the desired extension of the blade;

monitoring said relative movement by a measuring device so as to determine when the linear marking has been spaced from the cutting edge a distance equal to the desired extension of the blade; and adjusting the foot of the microkeratome until it is aligned with the linear marking.

10. A method in accordance with claim 9 in which said causing of the relative movement includes moving the magnifying device in a direction perpendicular to the linear marking.

11. A method in accordance with claim 10 in which said moving of said magnifying device is effected by a screw mechanism.

12. A method in accordance with claim 9 in which said monitoring of the relative movement is performed by an encoder.

13. A method in accordance with claim 9 in which said causing of the relative movement includes moving the microkeratome assembly in a direction perpendicular to the linear marking.

14. A method in accordance with claim 9 in which said causing and measuring of the relative movement is effected by a micrometer.

15. A method in accordance with claim 9 in which said adjusting of the foot is effected by operating a differential screw mechanism.

* * * * *